(12) United States Patent
Lenneman et al.

(10) Patent No.: US 11,266,416 B2
(45) Date of Patent: Mar. 8, 2022

(54) AORTIC OCCLUSION DEVICE

(71) Applicants: BOSTON SCIENTIFIC SCIMED, INC., Maple Grove, MN (US); REGENTS OF THE UNIVERSITY OF MINNESOTA, Minneapolis, MN (US)

(72) Inventors: Tina Marie Lenneman, Otsego, MN (US); Dennis A. Boismier, Shorewood, MN (US); Kyle Harish Srivastava, Saint Paul, MN (US); Kevin J. Goodwin, Minneapolis, MN (US); Felix Landaeta, Minneapolis, MN (US); Paige V. Tracy, South St. Paul, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 132 days.

(21) Appl. No.: 16/562,076

(22) Filed: Sep. 5, 2019

(65) Prior Publication Data
US 2020/0069312 A1 Mar. 5, 2020

Related U.S. Application Data
(60) Provisional application No. 62/727,256, filed on Sep. 5, 2018.

(51) Int. Cl.
*A61B 17/12* (2006.01)
*A61F 2/01* (2006.01)
*A61B 17/34* (2006.01)

(52) U.S. Cl.
CPC .. *A61B 17/12109* (2013.01); *A61B 17/12136* (2013.01); *A61F 2/013* (2013.01); *A61B 17/1204* (2013.01); *A61B 17/3421* (2013.01)

(58) Field of Classification Search
CPC ........ A61B 17/12109; A61B 17/12136; A61B 17/3421; A61B 17/1204; A61B 17/12009;
(Continued)

(56) References Cited

U.S. PATENT DOCUMENTS 6,036,706 A * 3/2000 Morejohn ............ A61B 17/122
606/157
6,042,563 A * 3/2000 Morejohn ........ A61B 17/12109
604/164.01
(Continued)

FOREIGN PATENT DOCUMENTS

EP 1060758 A1 12/2000
WO 2014186413 A2 11/2014

OTHER PUBLICATIONS

Shoyer et al.; "Five-year Outcomes After On-Pump and Off Pump Coronary-Artery Bypass." New England Journal of Medicine, 377. 7, 623-632, 2017.

*Primary Examiner* — Jocelin C Tanner
(74) *Attorney, Agent, or Firm* — Seager, Tufte and Wickhem, LLP

(57) ABSTRACT

A vessel occlusion device is provided for use during a coronary artery bypass procedure. The vessel occlusion device may include a clamp including at least one rigid portion sized to be disposed around an outer surface of a vessel such as the aorta. The clamp defines a clamp lumen sized to receive the vessel. The clamp has a sidewall with an opening extending therethrough, and an inflatable balloon disposed within the clamp lumen and positioned proximal of the opening in the sidewall.

18 Claims, 12 Drawing Sheets

(58) Field of Classification Search
CPC . A61B 17/12; A61B 17/0206; A61B 17/1325; A61B 2017/1205; A61B 2017/00876; A61B 2017/00477; A61B 2090/065; A61F 2/01; A61F 2/013; A61F 2002/016; A61M 25/1027; A61M 25/1011; A61M 2025/1015

See application file for complete search history.

(56) References Cited

U.S. PATENT DOCUMENTS

| | | | |
|---|---|---|---|
| 6,117,105 A * | 9/2000 | Bresnaham | A61B 17/12045 604/500 |
| 6,135,981 A | 10/2000 | Dyke | |
| 6,592,546 B1 | 7/2003 | Barbut et al. | |
| 7,645,285 B2 * | 1/2010 | Cosgrove | A61B 17/1227 606/151 |
| 7,998,153 B2 | 8/2011 | Kassab et al. | |
| 8,246,639 B2 * | 8/2012 | Kassab | A61B 17/122 606/158 |
| 2001/0053921 A1 * | 12/2001 | Jang | A61F 2/013 606/200 |
| 2004/0162519 A1 | 8/2004 | Helkowski et al. | |
| 2010/0081990 A1 * | 4/2010 | Swisher | A61J 15/0042 604/101.05 |
| 2011/0208218 A1 * | 8/2011 | Ball | A61B 17/1114 606/153 |
| 2013/0116654 A1 | 5/2013 | Dehdashtian et al. | |
| 2015/0257756 A1 * | 9/2015 | Sauer | A61B 17/0483 606/150 |

* cited by examiner

AORTIC OCCLUSION DEVICE

CROSS-REFERENCE TO RELATED APPLICATIONS

This application claims the benefit of priority under 35 U.S.C. § 119 to U.S. Provisional Application Ser. No. 62/727,256, filed Sep. 5, 2018, the entirety of which is incorporated herein by reference.

TECHNICAL FIELD

The present disclosure pertains to medical devices, and methods for manufacturing medical devices. More particularly, the present disclosure pertains to medical devices for occluding blood vessels.

BACKGROUND

Mortality rates have been shown to be improved for coronary artery bypass graft (CABG) when the patient is put on a bypass pump. However, current methods of clamping the aorta to put the patient on a bypass pump, such as using a cross clamp, generally deform the aorta, risking aortic dissection and dislodging emboli and putting the patient at risk for stroke. An alternative to the external cross clamp is the use of an aortic occlusion balloon, however these internal balloons may cause trauma including wall dissection or rupture due to distention of the aorta especially in older patients with thin walled aortas. There is thus a need for a way for cardiac surgeons to prevent trauma to the aorta during on-pump CABG procedures in order to decrease the risk of aortic dissection and emboli.

BRIEF SUMMARY

This disclosure provides design, material, manufacturing method, and use alternatives for medical devices. An example vessel occlusion device comprises a rigid clamp configured to be disposed around an outer surface of a vessel, the clamp defining a clamp lumen sized to receive the vessel, the clamp having a sidewall with an opening extending therethrough, and an inflatable balloon disposed within the clamp lumen.

Alternatively or additionally to the embodiment above, the clamp includes first and second clamp portions reversibly connected to one another, wherein the first and second clamp portions define the clamp lumen when connected.

Alternatively or additionally to the embodiment above, the first and second clamp portions include a magnetic connection element.

Alternatively or additionally to the embodiment above, the vessel occlusion device further comprises a liner disposed on an inner surface of the clamp.

Alternatively or additionally to the embodiment above, the liner is deformable.

Alternatively or additionally to the embodiment above, the liner includes an inflatable member.

Alternatively or additionally to the embodiment above, the vessel occlusion device further comprises a balloon plug configured to hold the balloon in a desired location within the vessel.

Alternatively or additionally to the embodiment above, the vessel occlusion device further comprises a balloon catheter attached to the balloon and extending through the balloon plug, the balloon catheter including an inflation lumen.

Alternatively or additionally to the embodiment above, the vessel occlusion device further comprises a cannula configured to fit through the opening in the clamp sidewall.

Alternatively or additionally to the embodiment above, the opening in the clamp sidewall is angled to direct the cannula to enter the vessel distal of the balloon.

Alternatively or additionally to the embodiment above, the clamp is a C shaped clamp with a hinge on one side.

Alternatively or additionally to the embodiment above, the C shaped clamp has a first rigid portion and a second flexible portion.

Alternatively or additionally to the embodiment above, the vessel occlusion device further comprising a pressure sensor disposed on an inner surface of the clamp.

Alternatively or additionally to the embodiment above, the vessel occlusion device further comprising a filter element connected to and disposed distal of the balloon.

Another example vessel occlusion device comprises first and second outer shells configured to be attached to one another and surround an outer surface of a vessel, the first outer shell having an opening extending through a wall defining the first outer shell, a deformable liner attached to inner surfaces of the first and second outer shells and an inflatable balloon configured to be disposed within the first and second outer shells.

Alternatively or additionally to the embodiment above, the vessel occlusion device further comprises a hinge connecting first sides of the first and second outer shells.

Alternatively or additionally to the embodiment above, the hinge is a spring hinge configured to bias the first and second outer shells in a closed orientation.

Alternatively or additionally to the embodiment above, the first and second outer shells each include a flange extending radially outward, wherein first and second magnets are disposed on respective flanges, the first and second magnets configured to hold the first and second outer shells together against a force created by inflation of the inflatable balloon.

Alternatively or additionally to the embodiment above, the vessel occlusion device further comprises a sensor configured to measure pressure applied to the vessel.

An example method of occluding the aorta during a coronary artery bypass procedure comprises inserting a balloon into the aorta, placing a clamp around an outer surface of the aorta over the balloon, wherein the clamp includes at least one rigid portion, the clamp having an opening extending through a sidewall of the rigid portion, wherein the clamp is placed around the aorta such that the opening is distal of the balloon, inflating the balloon to occlude the aorta, and inserting a cannula through the opening and into the aorta distal of the balloon.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
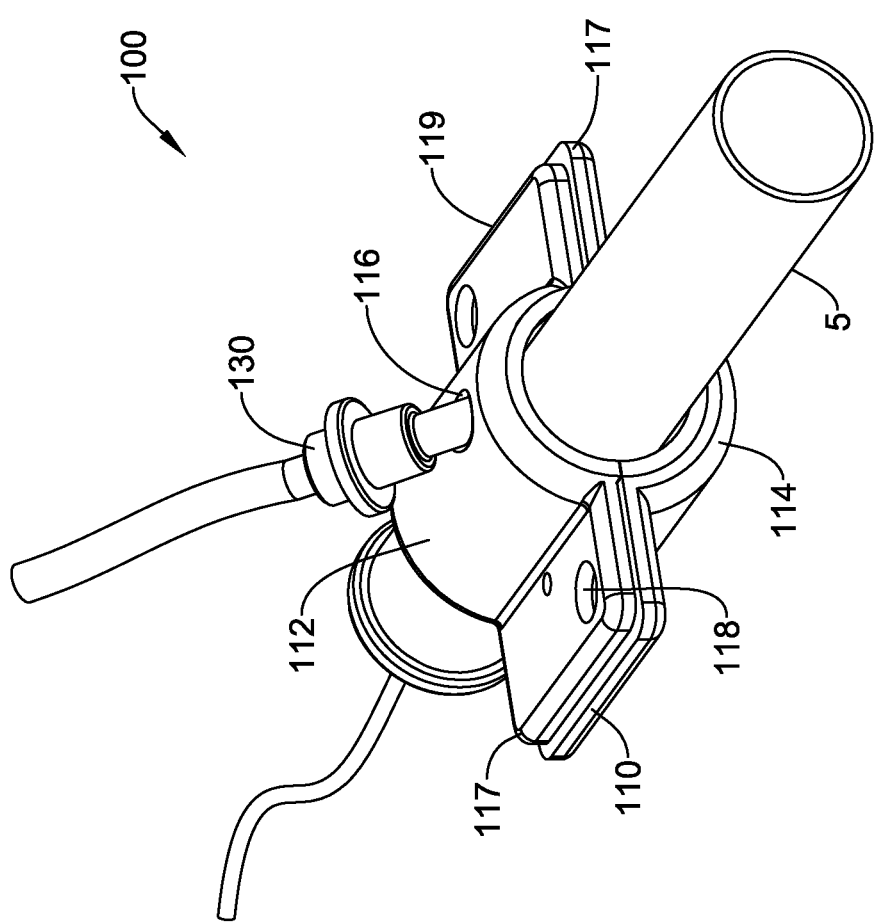
FIG. 1 is a perspective view of an example vessel occlusion device disposed on a vessel.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

FIG. 1 illustrates an example vessel occlusion device 100 in place over a blood vessel 5. The vessel occlusion device 100 may include a clamp 110 configured to be disposed around the outer surface of a blood vessel 5, such as the aorta. The clamp 110 may be rigid in order to protect the vessel 5 during occlusion, in particular, to prevent the vessel 5 from becoming distended. While the clamp 110 may surround the vessel 5, the clamp 110 does not compress the vessel 5. In some examples, the clamp 110 may include a first clamp portion 112 and a second clamp portion 114 configured to be attached to one another around the vessel 5. The first and second clamp portions 112, 114 may have at least one connection element 118 configured to reversibly connect the first and second clamp portions 112, 114. In some embodiments, the connection element 118 may include at least one magnet. A magnetic connection element 118 may provide a fast and secure connection holding the first and second clamp portions 112, 114 together. The magnetic connection element 118 may include an electromagnet and a metal member, and the vessel occlusion device 100 may include a controller configured to engage and disengage the electromagnet. In other embodiments, the connection element 118 may include at least one screw, snap fit connector, clasp, ratchet connection, or hook and loop connector. In some embodiments, the clamp 110 may include at least one flange 117 extending radially outward from one or both sides of the first and second clamp portions 112, 114. The flange 117 may include a hinge 119 pivotally connecting the first and second clamp portions 112, 114. In embodiments with a hinge 119 connecting first sides of the first and second clamp portions 112, 114, the connection element 118 may be disposed on the second side, opposite from the hinge.

Figure 2:
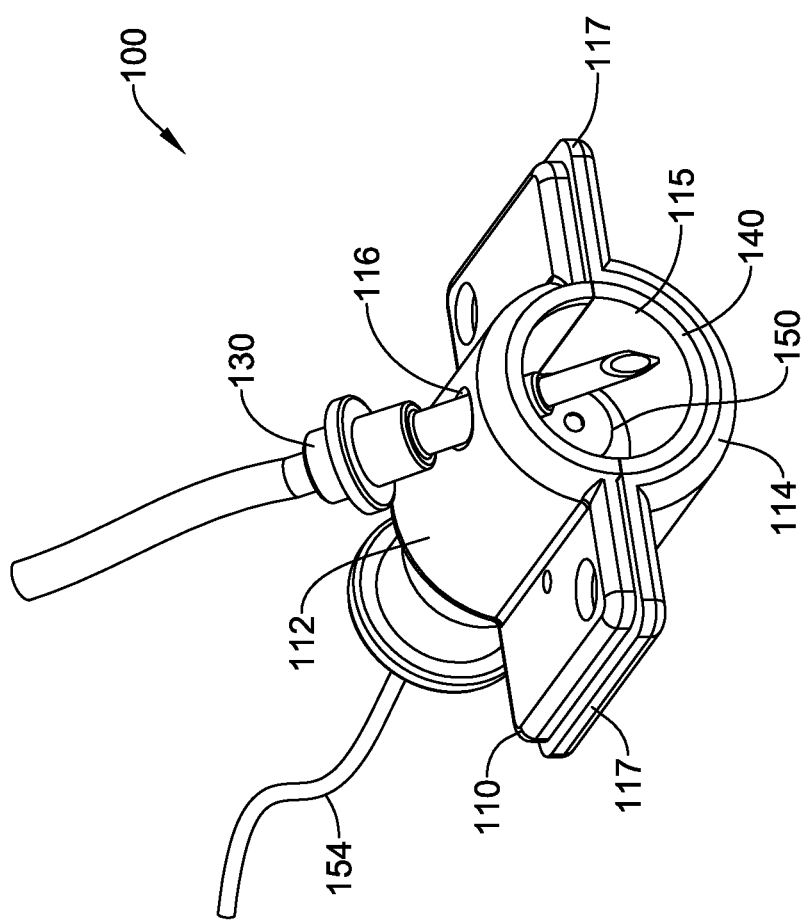
FIG. 2 is a perspective view of the vessel occlusion device of FIG. 1 without the vessel.

The clamp 110 may have an opening 116 extending radially through a sidewall of the clamp 110 and into the interior of the clamp 110. The opening 116 may allow for a cannula 130 to be inserted through the opening 116, into the interior of the clamp 110, and into the vessel 5. As shown in FIG. 2, the clamp 110 may define a lumen 115. The lumen 115 may have a diameter sized to receive the vessel 5 in a non-compressed state. The vessel 5 is not shown in FIG. 2 for clarity. For example, the lumen 115 may have a diameter of 20-40 mm to accommodate the human aorta. The vessel occlusion device 100 may further include an inflatable balloon 150 and attached inflation catheter 154 configured to be disposed inside the vessel. The balloon 150 may be disposed on the distal end of the inflation catheter 154. In some embodiments, the balloon 150 may be formed integral with the inflation catheter 154, such as being formed as a monolithic structure. Alternatively, the balloon 150 may be formed separately from the inflation catheter 154 and attached to the distal end thereof. The inflation catheter 154 may include an inflation lumen for inflating and deflating the balloon 150. The vessel 5 is occluded when the balloon 150 is inflated, and the clamp 110 is disposed on the outside of the vessel 5 in the region of the balloon 150, thereby preventing distention of the vessel 5 by the balloon 150. In some embodiments, a single balloon 150 is disposed on the inflation catheter 154, and the opening 116 is positioned through a distal region of the clamp 110 such that when the clamp 110 is placed over the vessel 5 and the balloon 150 is inflated, the opening is located distal of the balloon 150.

In some embodiments, the inner surface of the clamp 110 may include a liner 140. The liner 140 may be made of a soft, deformable material to cushion the vessel 5 when the clamp 110 is attached to the vessel 5. In some embodiments, the liner 140 may be a gel, foam, or elastomeric material. In other embodiments, the liner 140 may include at least one inflatable member attached to the inner surface of the clamp 110. An inflatable liner 140 may be connected to the inflation catheter 154. The balloon 150 and inflatable liner 140 may be inflated simultaneously. In other embodiments, the balloon 150 and the inflatable liner 140 may have separate inflation lumens allowing separate and independent inflation. The pressure applied to the vessel 5 is equalized between the liner 140 and balloon 150, minimizing damage to the vessel 5 and preventing vessel distention.

Figure 3:
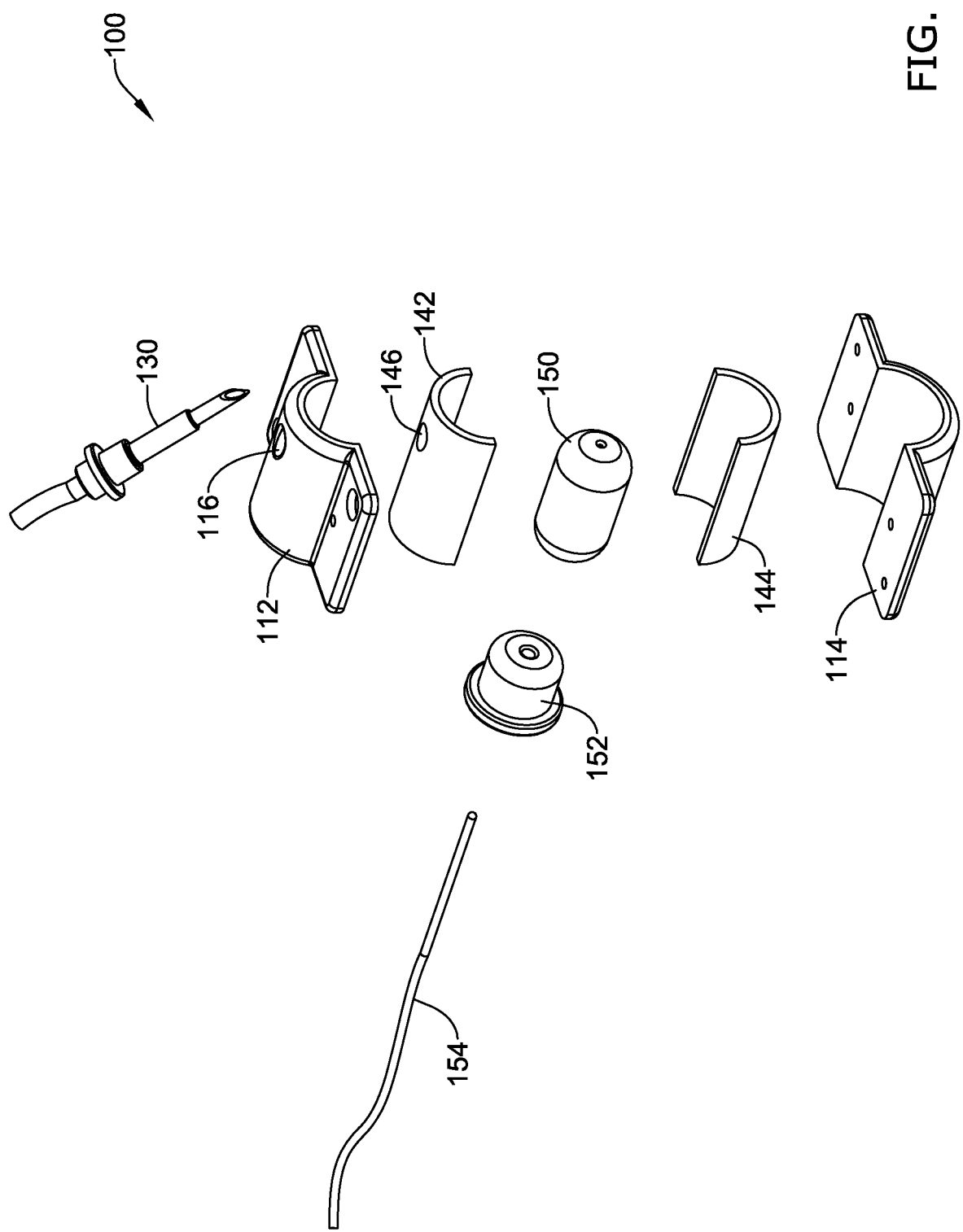
FIG. 3 is an exploded view of the vessel occlusion device of FIG. 2.

As shown in FIG. 3, in some embodiments, the liner 140 may be formed as a first liner member 142 attached to the inner surface of the first clamp portion 112, and a second liner member 144 attached to the inner surface of the second clamp portion 114. As discussed above, the first and second liner members 142, 144 may be sections of deformable material or they may be separate inflatable members. The first liner member 142 may include an opening 146 therethrough that aligns with the opening 116 in the first clamp portion 112. The inflatable balloon 150 may be connected to a balloon plug 152 configured to retain the balloon 150 in place.

Figure 4:
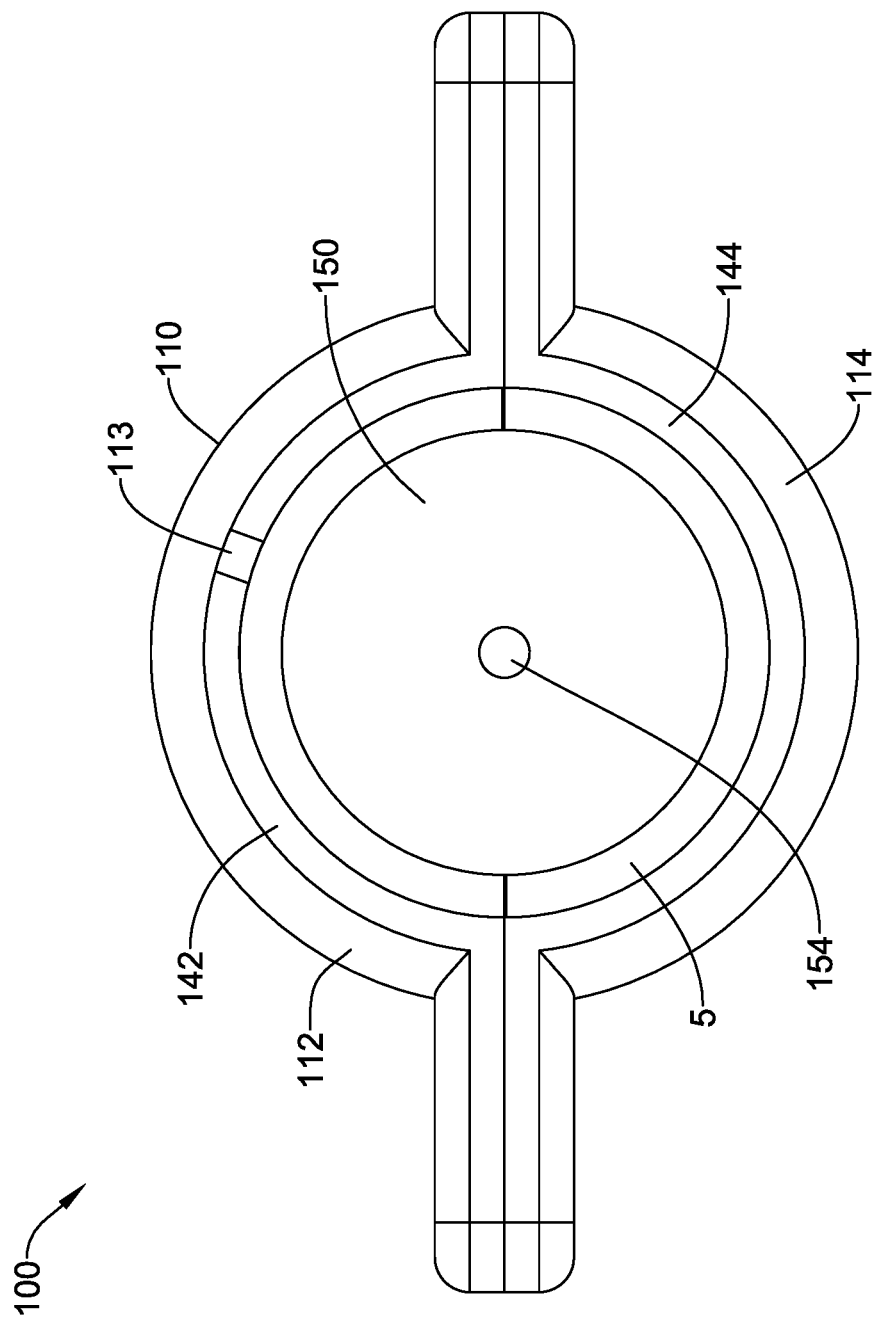
FIG. 4 is a front cross sectional view of the vessel occlusion device of FIG. 1.

FIG. 4 is a front cross sectional view of the vessel occlusion device 100 disposed over a vessel 5. The first and second clamp portions 112, 114 surround the vessel 5 with the first and second liner members 142, 144 contacting the outer surface of the vessel 5. The inflated balloon 150 is disposed inside the vessel 5, securing the vessel against the first and second liner members 142, 144 and occluding the vessel 5. In contrast to the conventional use of a cross clamp, the vessel occlusion device 100 is configured to occlude the vessel 5 without significantly altering the vessel's shape and size, thereby reducing vessel injury. The inflation of the balloon 150 may be regulated to a level sufficient to occlude the vessel 5 but without compressing the vessel wall, thereby preventing damage to the vessel 5. The vessel occlusion device 100 prevents distention of the vessel 5, and may generate only about 2% of the pressure generated by conventional cross clamps when used on the aorta. In some embodiments, the vessel occlusion device 100 may include a sensor 113. The sensor 113 may be a pressure sensor configured to detect the pressure exerted on the vessel 5. The sensor 113 may be connected to a control mechanism regulating the inflation of the balloon 150, where the control mechanism may regulate the inflation of the balloon 150 to adjust the pressure being applied to the vessel 5. In some embodiments, the sensor 113 may be disposed on an inner surface of the clamp 110. If a liner 140 is present, the liner 140 may have an opening to accommodate the sensor 113. The sensor 113 may alternatively be disposed on the inner surface of the liner 140. In other embodiments, the sensor 113 may be disposed on the outer surface of the balloon 150.

Figure 5:
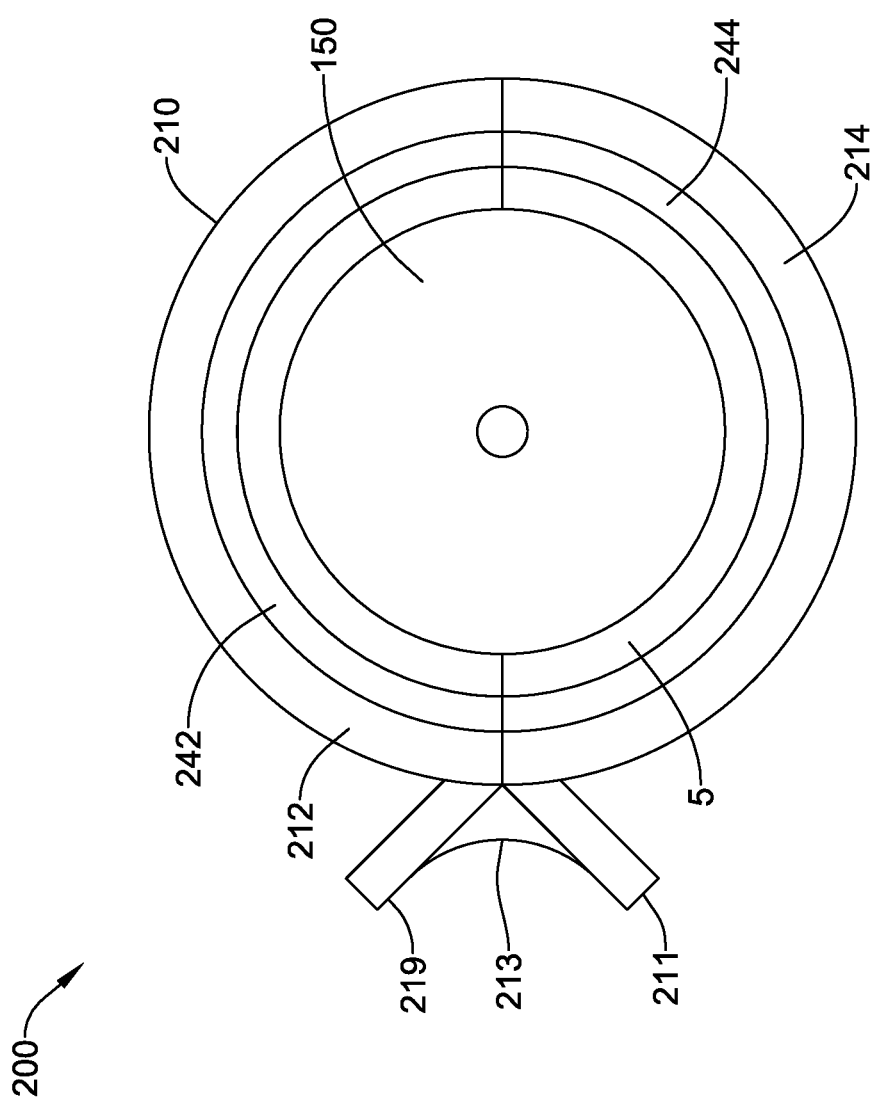
FIG. 5 is a front cross sectional view of an example vessel occlusion device disposed on a vessel.

In some embodiments, the vessel occlusion device 200 may include a C shaped external clamp 210 having first and second clamp portions 212, 214 connected by a hinge 219, as shown in FIG. 5. The clamp 210 may be disposed over the outer surface of the vessel 5 and may be used with the balloon 150 as discussed above. In some embodiments, the hinge 219 may be a spring hinge and may include first and second gripping members 211 connected by a spring 213. The spring hinge may be configured to bias the first and second clamp portions 212, 214 in the closed configuration as shown in FIG. 5. Applying a force by pinching the first and second gripping members 211 together overcomes the spring bias and separates the first and second clamp portions 212, 214. The first and second clamp portions 212, 214 may include first and second liner portions 242, 244 which may be made of a soft, deformable material such as a gel, foam, or elastomeric material. In other embodiments, the first and second liner portions 242, 244 may include one or more inflatable members attached to the inner surface of the first and second clamp portions 212, 214. In use, the first and second gripping members 211 are pinched together, compressing the spring 213 and opening the first and second clamp portions 212, 214 so the vessel occlusion device 200 may be disposed around the vessel 5. The balloon 150 may then be inflated to occlude the vessel 5.

Figure 6:
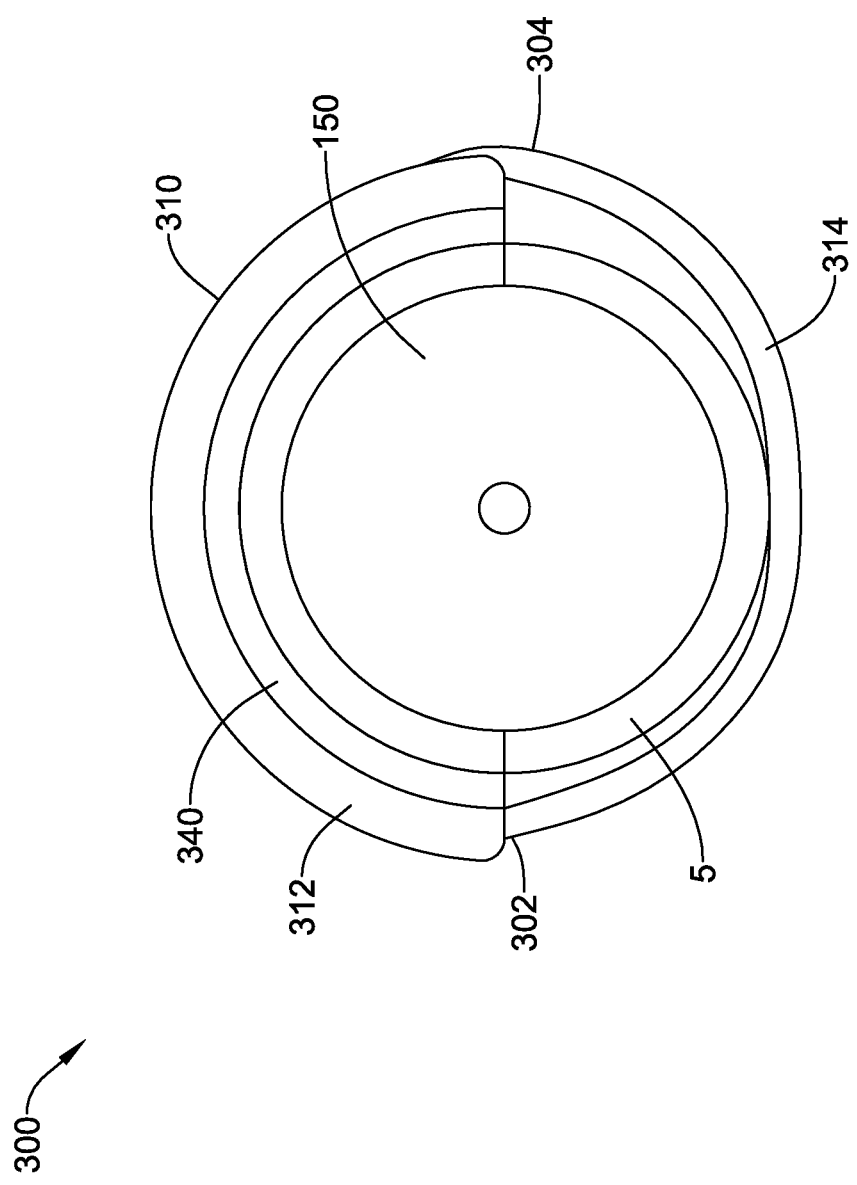
FIG. 6 is a front cross sectional view of an example vessel occlusion device disposed on a vessel.

In another embodiment, an exterior C shaped clamp 310 of the vessel occlusion device 300 may include a first rigid curved portion 312 connected to a second flexible portion, as shown in FIG. 6. The clamp 310 may be disposed over the outer surface of the vessel 5 and may be used with the balloon 150 as discussed above. The second flexible portion may be a strap 314 having a first end 302 permanently attached to one side of the rigid curved portion 312 and a second end 304 removably attached to an opposite side of the rigid curved portion 312. The strap 314 may be made of a woven or knit fabric. The strap 314 may be a non-stretch or stretchy fabric. In other embodiments, the strap 314 may be a woven or knit metal mesh. The second end 304 of the strap 314 may be attached to the rigid curved portion 312 with a snap attachment, hook and eye, hook and loop attachment, or other removable attachment member. In some embodiments, the rigid curved portion 312 may have a liner 340 that may be made of a soft, deformable material such as a gel, foam, or elastomeric material. In other embodiments, the liner 340 may include an inflatable member attached to the inner surface of the rigid curved portion 312. In use, the rigid curved portion 312 may be placed over the top of the vessel 5 and the strap 314 wrapped around the vessel 5 with the second end 304 of the strap 314 attached to the rigid curved portion 312. The balloon 150 may then be inflated to occlude the vessel 5.

Figure 7:
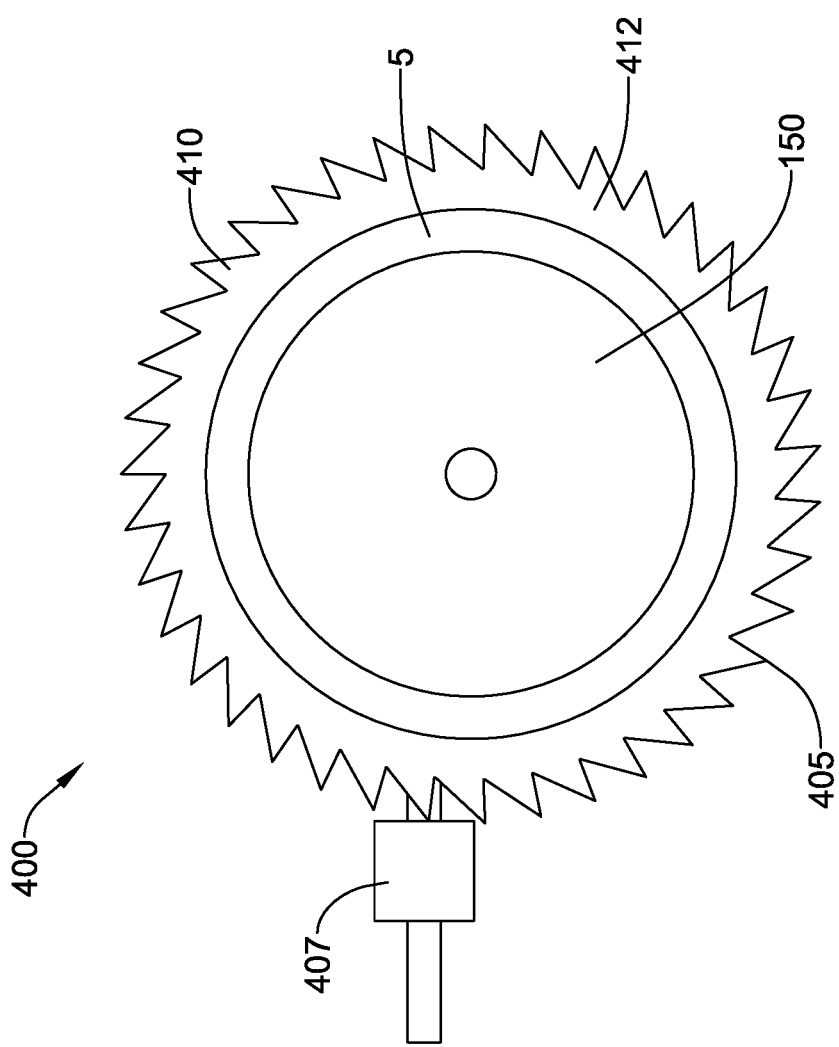
FIG. 7 is a front cross sectional view of an example vessel occlusion device disposed on a vessel.

In a further embodiment, the vessel occlusion device 400 may include an exterior clamp 410 defined by a flexible band 412 with a plurality of projections 405 on an outer surface thereof, as shown in FIG. 7. The clamp 410 may be disposed over the outer surface of the vessel 5 and may be used with the balloon 150 as discussed above. A connector 407 disposed on a first end of the band 412 may be configured to receive the second end of the band 412 and releasably hold the band 412. In some embodiments, the connector 407 engages the projections 405, similar to a zip tie. The flexible band 412 may be made of a flexible polymer, plastic, or metal material. In use, the flexible band 412 may be placed around the vessel 5 with the second end threaded through the connector 407. The band 412 may be cinched until the inner surface of the band 412 engages the outer surface of the vessel 5. The balloon 150 may then be inflated to occlude the vessel 5.

Figure 8:
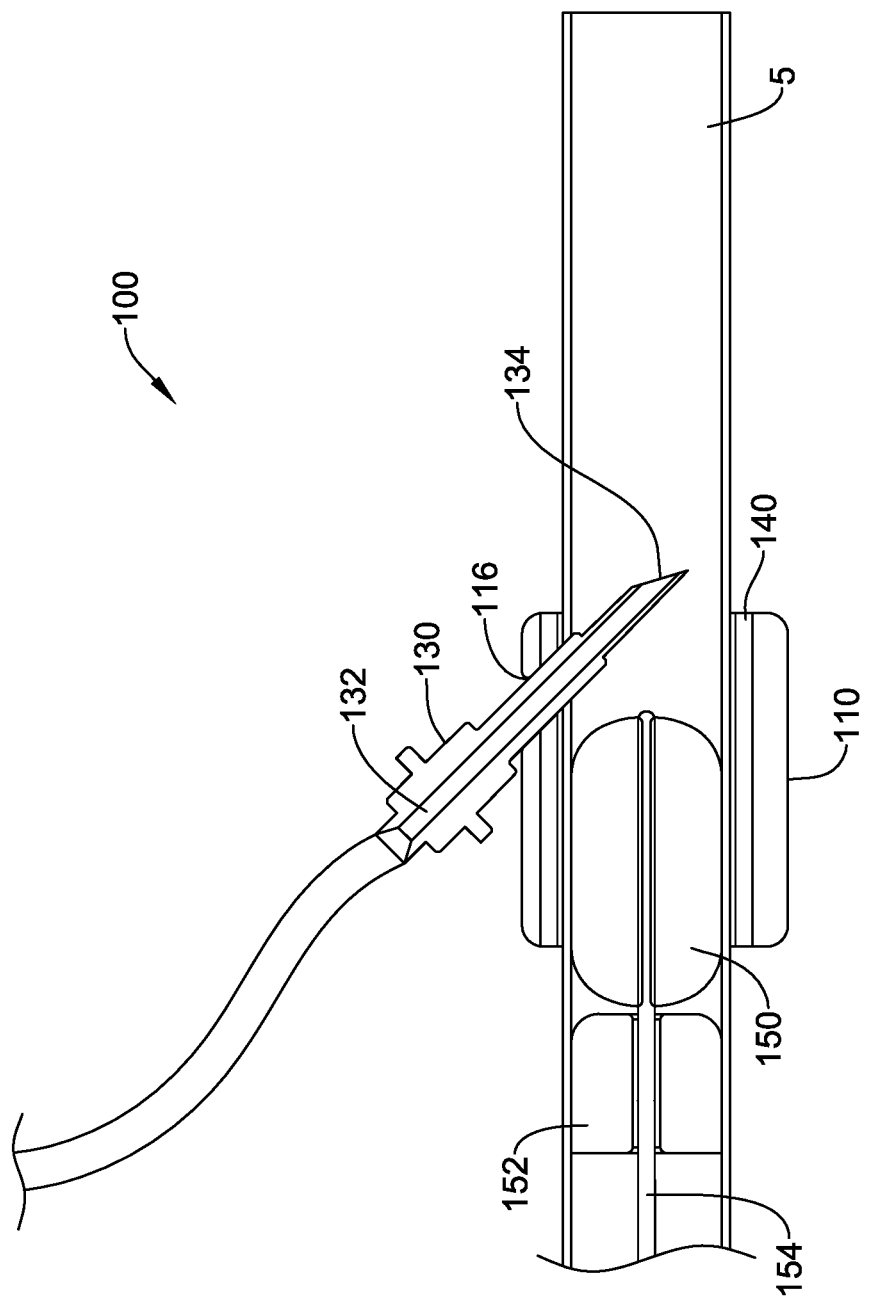
FIG. 8 is a side cross sectional view of the vessel occlusion device of FIG. 1 in place over a vessel.

In use, during a coronary artery bypass graft procedure, the patient is put on the bypass machine, and then the balloon 150 and balloon plug 152 may be passed through the vasculature to the occlusion site, which may be within a vessel 5 such as the aorta, distal to the aortic valve and proximal to the brachiocephalic artery. Alternatively, the balloon 150 may be inserted directly into the vessel 5 via a surgical procedure. The clamp 110 may then be placed around the aorta 5 with the liner 140 in contact with the aorta. The clamp 110 may be placed over the location of the balloon 150 with the opening 116 positioned distal of the balloon 150, as shown in FIG. 8. Inflation media may then be delivered through the inflation catheter 154 to inflate the balloon 150 until the aorta is occluded. A cannula 130 with an inner lumen 132 and a sharpened distal tip 134 may be inserted through the opening 116 in the clamp 110 and liner 140 and into the vessel 5. The opening 116 in the clamp 110 may be angled to direct the cannula 130 away from and distal of the balloon 150, as shown in FIG. 8. The cardiovascular surgical procedure is then performed. Oxygenated blood may be delivered through the cannula 130 distal of the occlusion, toward the aortic arch. After the procedure is completed, the balloon 150 is deflated and removed and the clamp 110 is removed, and the patient is removed from the bypass machine.

Figure 9:
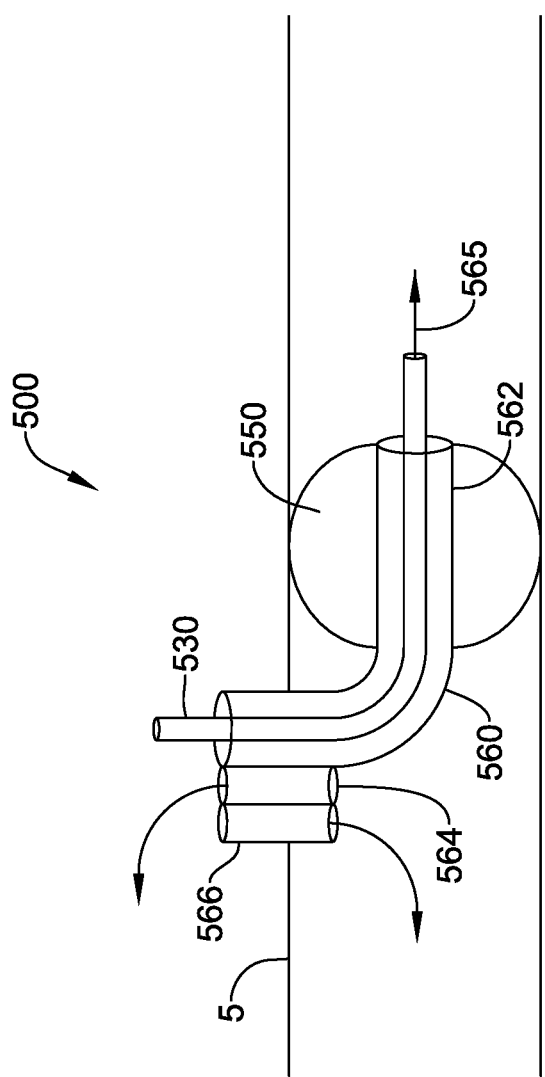
FIG. 9 is a cross sectional view of an example vessel occlusion device in a vessel.

An alternate vessel occlusion device 500 may include a multi-lumen catheter 560 having a balloon 550 attached around a central lumen 562 at a distal end of the catheter 560, as shown in FIG. 9. The central lumen 562 may be sized to receive a conventional cannula 530 configured to deliver oxygenated blood, indicated by arrow 565, to a location distal of the balloon 550. The multi-lumen catheter 560 may include additional lumens such as a vent lumen 564 facing towards the aortic valve to vent air bubbles from the left side of the heart, and a cardioplegia solution lumen 566 configured to deliver cardioplegia solution towards the aortic valve to arrest heart motion during bypass. Inflation of the balloon 550 occludes the aorta 5. In some embodiments, one of the clamps 110, 210, 310, 410 described above may be placed around the aorta 5 in the location of the balloon 550.

Figure 10:
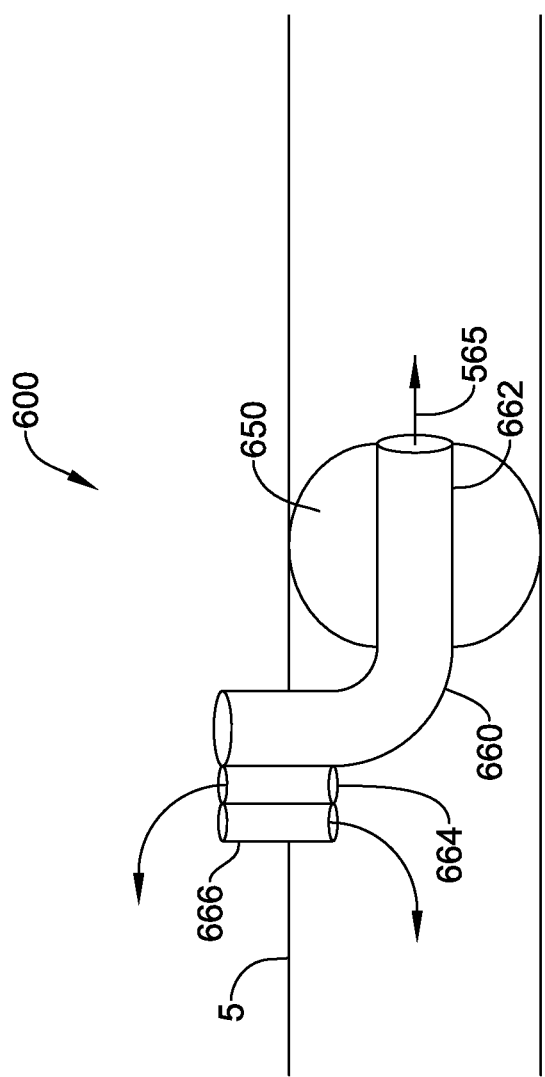
FIG. 10 is a cross sectional view of an example vessel occlusion device in a vessel.

In some embodiments, a vessel occlusion device 600 may include a multi-lumen catheter 660 having a balloon 650 attached around a central lumen 662 at a distal end of the catheter 660, as shown in FIG. 10. The central lumen 662 may itself be configured to deliver oxygenated blood, indicated by arrow 565, to a location distal of the balloon 650. The multi-lumen catheter 660 may include additional lumens such as a balloon inflation lumen (not shown), a vent lumen 664 facing towards the aortic valve to vent air bubbles from the left side of the heart, and a cardioplegia solution lumen 666 configured to deliver cardioplegia solution towards the aortic valve. Inflation of the balloon 650 occludes the aorta 5. In some embodiments, one of the clamps 110, 210, 310, 410 described above may be placed around the aorta 5 in the location of the balloon 650.

Figure 11:
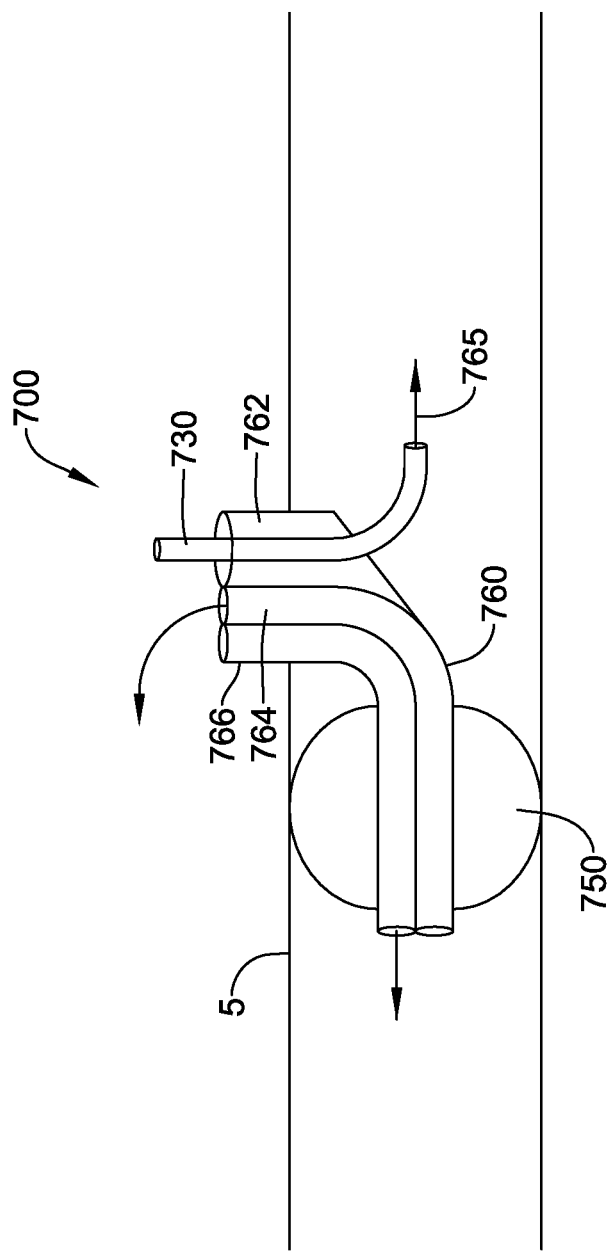
FIG. 11 is a cross sectional view of an example vessel occlusion device in a vessel.

In some embodiments, a vessel occlusion device 700 may include a multi-lumen catheter 760 having a cannula lumen 762 configured to receive a conventional cannula 730, a vent lumen 764 facing towards the aortic valve to vent air bubbles from the left side of the heart, and a cardioplegia solution lumen 766 configured to deliver cardioplegia solution towards the aortic valve, as shown in FIG. 11. A balloon 750 may be disposed around the vent lumen 764 and the cardioplegia solution lumen 766, and be configured to be disposed pointed in the direction of the aortic valve. The cannula lumen 762 may be configured to receive the cannula 730 to deliver oxygenated blood in a direction away from the aortic valve, indicated by arrow 765. Inflation of the balloon 750 via an inflation lumen (not shown) in the multi-lumen catheter 760 occludes the aorta 5. In some embodiments, one of the clamps 110, 210, 310, 410 described above may be placed around the aorta 5 in the location of the balloon 750.

Figure 12:
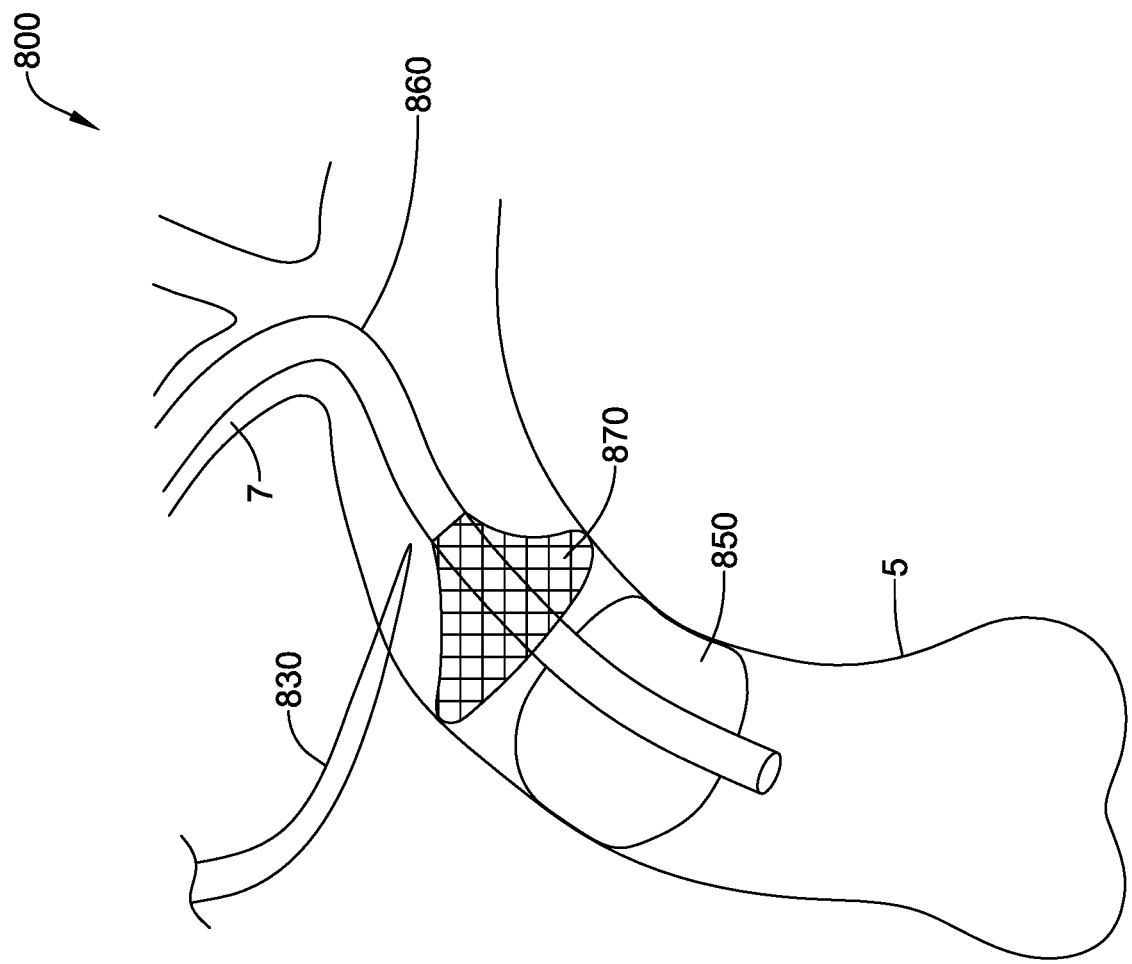
FIG. 12 is a cross sectional view of an example vessel occlusion device and filter in a vessel.

FIG. 12 shows an example vessel occlusion device 800 that may include a balloon 850 and filter 870 disposed adjacent one another on a catheter 860. The catheter 860 may include an inflation lumen (not shown) for inflating the balloon 850. The vessel occlusion device 800 may be used in a transcatheter approach from the right subclavian artery 7. The balloon 850 may be disposed adjacent the distal end of the catheter 860 and may be positioned with the aorta 5 in a direction towards the aortic valve. The catheter 860 may allow positioning of the balloon 850 in the ascending aorta and provide embolic protection with the filter 870 distal of the balloon 850 occlusion. In use, a cannula 830 may be inserted into the aorta 5 distal to the filter to provide inflow of oxygenated blood. In some embodiments, one of the clamps 110, 210, 310, 410 described above may be placed around the aorta 5 in the location of the balloon 850. The filter 870 may be included in any of the vessel occlusion devices 100, 200, 300, 400, 500, 600, 700 discussed above, located distal of the balloon.

The elements of the vessel occlusion device 100, 200, 300, 400, 500, 600, 700, 800 may be made of a variety of materials. In the following discussion the vessel occlusion device 100 and clamp 110 will be referenced, however it will be understood that the materials discussed will apply to the elements in any embodiment of vessel occlusion device 100, 200, 300, 400, 500, 600, 700, 800. Some suitable but non-limiting materials that can be used for the various components of the vessel occlusion device 100 including the clamp 110, liner 140, balloon 150 (and/or other systems disclosed herein) and the various elements thereof disclosed herein may include those commonly associated with medical devices.

In some embodiments, the clamp 110 and/or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, 314LV, 304, or 316 stainless steel; mild steel; nickel-titanium alloy such as linear-elastic and/or super-elastic nitinol; other nickel alloys such as cobalt-chromium-tungsten-nickel alloy (e.g., UNS: R30605 such as L605®), nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In some embodiments, the clamp 110 and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the catheter can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A vessel occlusion device comprising:
    a rigid clamp configured to be disposed around an outer surface of a vessel, the clamp defining a clamp lumen sized to receive the vessel, the clamp having a sidewall with an opening extending therethrough;
    an inflatable balloon disposed within the clamp lumen; and
    a cannula configured to fit through the opening in the clamp sidewall;
    wherein the opening is angled to direct the cannula to enter the vessel distal of the balloon.

2. The vessel occlusion device of claim 1, wherein the clamp includes first and second clamp portions reversibly connected to one another, wherein the first and second clamp portions define the clamp lumen when connected.

3. The vessel occlusion device of claim 2, wherein the first and second clamp portions include a magnetic connection element.

4. The vessel occlusion device of claim 1, further comprising a liner disposed on an inner surface of the clamp.

5. The vessel occlusion device of claim 4, wherein the liner is deformable.

6. The vessel occlusion device of claim 5, wherein the liner includes an inflatable member.

7. The vessel occlusion device of claim 1, further comprising a balloon plug configured to hold the balloon in a desired location within the vessel.

8. The vessel occlusion device of claim 7, further comprising a balloon catheter attached to the balloon and extending through the balloon plug, the balloon catheter including an inflation lumen.

9. The vessel occlusion device of claim 1, wherein the clamp is a C shaped clamp with a hinge on one side.

10. The vessel occlusion device of claim 9, wherein the C shaped clamp has a first rigid portion and a second flexible portion.

11. The vessel occlusion device of claim 1, further comprising a pressure sensor disposed on an inner surface of the clamp.

12. The vessel occlusion device of claim 1, further comprising a filter element connected to and disposed distal of the balloon.

13. A vessel occlusion device comprising:
    first and second outer shells configured to be attached to one another and surround an outer surface of a vessel, the first outer shell having an opening extending through a wall defining the first outer shell;
    a deformable liner attached to inner surfaces of the first and second outer shells;
    an inflatable balloon configured to be disposed within the first and second outer shells; and
    a cannula configured to fit through the opening in the first outer shell;
    wherein the opening is angled to direct the cannula to enter the vessel distal of the balloon.

14. The vessel occlusion device of claim 13, further comprising a hinge connecting first sides of the first and second outer shells.

15. The vessel occlusion device of claim 14, wherein the hinge is a spring hinge configured to bias the first and second outer shells in a closed orientation.

16. The vessel occlusion device of claim 13, wherein the first and second outer shells each include a flange extending radially outward, wherein first and second magnets are disposed on respective flanges, the first and second magnets configured to hold the first and second outer shells together against a force created by inflation of the inflatable balloon.

17. The vessel occlusion device of claim 13, further comprising a sensor configured to measure pressure applied to the vessel.

18. A method of occluding the aorta during a coronary artery bypass procedure, the method comprising:
    inserting a balloon into the aorta;
    placing a clamp around an outer surface of the aorta over the balloon, wherein the clamp includes at least one rigid portion, the clamp having an opening extending through a sidewall of the rigid portion, wherein the clamp is placed around the aorta such that the opening is distal of the balloon;
    inflating the balloon to occlude the aorta; and
    inserting a cannula through the opening and into the aorta distal of the balloon.

* * * * *